US007494773B2

(12) United States Patent
McCready et al.

(10) Patent No.: US 7,494,773 B2
(45) Date of Patent: Feb. 24, 2009

(54) NUCLEOTIDE SEQUENCES SPECIFIC TO BRUCELLA AND METHODS FOR THE DETECTION OF BRUCELLA

NUCLEOTIDE SEQUENCES SPECIFIC TO *BRUCELLA* AND METHODS FOR THE DETECTION OF *BRUCELLA*

RELATED APPLICATION

This application claims the benefit of U.S. Provisional Application No. 60/400,891, filed Aug. 1, 2002, and entitled, "DNA Diagnostics *Brucella* Species," which is incorporated herein by this reference.

The United States Government has rights in this invention pursuant to Contract No. W-7405-ENG-48 between the United States Department of Energy and the University of California for the operation of Lawrence Livermore National Laboratory.

GENE SEQUENCE LISTING IN COMPUTER READABLE FORM

The sequence listing information recorded in computer readable form is identical to the written on paper sequence listing.

BACKGROUND

*Brucella* is the species of bacteria known to cause what is commonly known as Brucellosis, a serious and sometimes fatal disease. Since the attack on the World Trade Center in New York of Sep. 11, 2001, there has been a growing concern that terrorists or rogue governments will use the *Brucella* bacterium as a weapon of mass destruction and instrument of terror. Since the events of Sep. 11, 2001, the United States Government has been developing reliable methods and systems to detect the *Brucella* bacterium so that immediate and effective counter measures can be undertaken. The existing methods for detecting the *Brucella* bacterium are considered inadequate because of the higher than acceptable rate of false positive and false negative results. False positive results lead to confusion regarding whether the *Brucella* bacterium is actually present and whether protective measures should immediately be implemented. Conversely, false negative results would allow the *Brucella* bacterium to remain undetected with consequent adverse impacts. A more reliable method of detecting the *Brucella* bacterium would reduce the occurrence of false positive and false negative results and provide decision makers with greater confidence in implementing appropriate counter measures.

SUMMARY OF THE INVENTION

This invention includes the nucleotide sequences that are identified in SEQ ID NOs:4, 8, 12, 16, 20 and 24 that are specific to *Brucella*.

Another aspect of the invention includes a Forward Primer, the nucleotide sequences that are identified in SEQ ID NOs:1, 5, 9, 13, 17 and 21, and any primers that are derived from these nucleotide sequences.

A further aspect of the invention is a Reverse Primer, the nucleotide sequences that are identified in SEQ ID NOs:2, 6, 10, 14, 18 and 22, and any primers that are derived from these nucleotide sequences.

A further aspect of the invention includes a Hybridization Probe, the nucleotide sequences that are identified in SEQ ID NOs:3, 7, 11, 15, 19 and 23, and any probes that are derived from these nucleotide sequences.

This invention also includes a method for the detection of *Brucella* using the bacterium specific nucleotide sequence comprising: providing a sample in an environment that is suitable for isolating genomic DNA for amplification using PCR and under conditions suitable for hybridization with a least one group of nucleotides consisting of a forward primer, a reverse primer and a hybridization probe and detecting the existence of *Brucella* specific nucleotide sequences by a nucleotide detection method, such as PCR and flurogenic 5' nuclease PCR assay, wherein the existence of the nucleotide sequence indicates the presence of *Brucella* in the sample.

BRIEF DESCRIPTION OF THE SEQUENCES

SEQ ID NO:1 Primer
SEQ ID NO:2 Primer
SEQ ID NO:3 Probe
SEQ ID NO:4 Amplicon
SEQ ID NO:5 Primer
SEQ ID NO:6 Primer
SEQ ID NO:7 Probe
SEQ ID NO:8 Amplicon
SEQ ID NO:9 Primer
SEQ ID NO:10 Primer
SEQ ID NO:11 Probe
SEQ ID NO:12 Amplicon
SEQ ID NO:13 Primer
SEQ ID NO:14 Primer
SEQ ID NO:15 Probe
SEQ ID NO:16 Amplicon
SEQ ID NO:17 Primer
SEQ ID NO:18 Primer
SEQ ID NO:19 Probe
SEQ ID NO:20 Amplicon
SEQ ID NO:21 Primer
SEQ ID NO:22 Primer
SEQ ID NO:23 Probe
SEQ ID NO:24 Amplicon

DETAILED DESCRIPTION

Disclosed herein are six nucleotide sequences located on different loci of the *Brucella* bacterium genome. Also disclosed, are primers and the hybridization probes used in detecting the specific nucleotide sequences as well as a method for identifying *Brucella* by analyzing samples taken from monitoring devices, such as air monitors, for the nucleotide sequences that are specific to *Brucella*. By using the primers and hybridization probes developed from the nucleotide sequences identified as unique to the *Brucella* bacterium to detect the presence of the *Brucella* bacterium, far more reliable results are obtained than by using existing methods. False positive and false negative results are greatly reduced.

Brucella is the bacterium that causes what is commonly known as Brucellosis, a disease that can cause can cause significant adverse health effects if not detected early and treated with appropriate antibiotics. Brucellosis is characterized by "a range of symptoms that are similar to the flu and may include fever, sweats, headaches, back pains, and physical weakness. Sever infections of the central nervous systems or lining of the heart may occur. Brucellosis cab [sic] also causes long-lasting or chronic symptoms that include recurrent fevers, joint pain, and fatigue." This information can be found at the website for the Center for Disease Control and Prevention (CDC). It is on the Center for Disease Control and Prevention (CDC) list of possible bacteria that has potential as a biological warfare weapon. The CDC has developed a list of possible pathogens that may be used as bioterrorism weapons. Brucella has been listed in Category B of possible diseases and agents. Those diseases and agents in Category B are considered a high risk to national security because. they "are moderately easy to disseminate; result in moderate morbidity rates and low mortality rates; and require specific enhancements of CDC's diagnostic capacity and enhanced disease surveillance." This information can be found at the CDC website A key element in developing defenses against the use of *Brucella* is the ability to quickly and accurately detect the presence of the bacterium. Early detection will allow for the implementation of effective counter measures. Additionally, early detection will allow for the identification and treatment of those that may have been exposed to the bacterium. Early detection and treatment is essential for the treatment of Brucellosis because significant adverse health effects, including death, may occur if it is not detected early and treated with antibiotics.

Existing detection methods have resulted in a higher than acceptable rate of false positive and false negative results. Such results are inadequate and can create confusion regarding the appropriate countermeasures, if any, that should be undertaken because it is unclear whether the bacterium is present or not. If the bacterium is not present, undertaking counter measures may cause undue expense and create unwarranted concern among those that may incorrectly believe they have been exposed.

Although the genome for *Brucella* has already been mapped, this alone was not sufficient to develop a reliable and accurate detection mechanism because the current methods use nucleotide sequences that may be common to many different bacteria. Thus, existing detection methods could not distinguish between various bacteria, which resulted in higher than acceptable false positive detection rates. Similarly, some existing detection methods resulted in false negative results because they were not sensitive enough to detect the bacterium.

Using a nucleotide sequence that is specific to the *Brucella* bacterium results in a more reliable detection method.

Six nucleotide sequences contained in SEQ ID NOs:4, 8, 12, 16, 20 and 24 are specific to *Brucella*. These sequences are known as "amplicons." The existence of these nucleotide sequences in a sample is conclusive proof that the bacterium *Brucella* is present. In order to detect any of the six amplicons specific to *Brucella*, a series of forward and reverse primers and hybridization probes were developed for each of the six amplicons.

The typical assay determines the presence of SEQ ID NOs:4 and 8 using the sequence specific primers and the hybridization probes. If there is a positive result for the presence of *Brucella* then an assay is run to determine the presence of additional amplicon sequences, as a means to double check for the presence of *Brucella*.

Once the *Brucella* specific nucleotide sequences were identified, the presence of the bacteria could be detected from environmental samples using PCR assay analysis and detection. PCR is a technique utilized to amplify genomic DNA. Typical PCR reactions include appropriate PCR buffers, nuclease polymerase and one or more oligonucleotide primers and hybridization probes. Various modifications of PCR techniques are possible as detailed in *Current Protocols in Molecular Biology* ed. F. M. Ausubel, R. Brent, D. D. Moore, K. Struhle, Massachusetts General Hospital and Harvard Medical School (1987), which is hereby incorporated by reference. The following US patents describe PCR and are incorporated herein by reference: U.S. Pat. No. 4,683,195; U.S. Pat. No. 4,683,202; U.S. Pat. No. 4,800,159.

One method that may be used for real-time PCR amplification and detection is TaqMan®. The principles involved in the conventional Taqman® 5' exonuclease assay are described in detail by Holland et al in, *Detection of specific polymerase chain reaction product by utilizing the 5'- - -3' exonuclease activity of Thermus aquaticus polynucleotide polymerase*, Proc Natl Acad Sci USA 88 (16):7276-80, 1991, which is herein incorporated by reference. TaqMan® real time detection can also be used to simultaneously detect a plurality of nucleic acid targets when it is used with multiplex PCR, which enables simultaneous detection of more than one target sequence, thus enhancing detection accuracy. A few examples of typical PCR instruments include the ABI prism 7700, the Cepheid Smart Cycler, and the Bio-Rad iCycler. In order to use a PCR assay method for detection of the *Brucella* bacterium, the sample must be prepared to extract all DNA that may be present. The following is a protocol for the preparation of samples taken from ambient air monitoring devices for nucleotide detection using fluorogenic 5' nuclease PCR assay.

Assay Protocol

Definitions:
 DNA—deoxyribonucleic acid
 EDTA—ethylenediaminetetraacetic acid
 PCR—polymerase chain reaction
 PCR water—autoclaved water, then filtered
 CT—cycle threshold—the cycle in which the fluorescence signal crosses a user defined threshold
 FAM—reporter dye
 TAMRA—quencher dye Sample Preparation:

Exposed environmental filter are suspended in Sodium phosphate/EDTA, Tween buffer and bead beaten. The supernatant is filtered and washed to yield the genomic DNA extract. The extract is then subjected to real-time polymerase chain reaction (PCR) assay using a fluorescent-labeled probe. This process monitors a PCR reaction and the quantity of double-stranded product that is produced Materials:
 1. A series of forward and reverse primers, a hybridization probe and polymerase reagents specific to the first amplicon to be detected.
 2. A series of forward and reverse primers, a hybridization probe and polymerase reagents specific to the second amplicon to be detected.
 3. Bead Beater Kit
 Bead beater kit includes:
  a. 3 capped tubes containing a filter and beads
  b. 3 yellow ultra free MC Centrifugal Filter Units
  c. 6 blue microcon YM-100 filter units
  d. 12 collection tubes
  e. 7 PCR reaction mix—includes primer/probe and Taq-labeled A, B, C, D, E, F, G
  f. 48-25 µl Smart Cycle reaction tubes
  g. Sodium phosphate buffer/EDTA Teen buffer
  h. PCR water
  i. Inhibitory control DNA
  j. Extra unlabeled tubes
 4. Cepheid Smart Cycle
 5. Microcentrifuge
 6. Microfuge for Cepheid tubes Preparation of DNA Extract:

Perform in segregated work areas and in a biosafety cabinet using BSL 2 practices.

1. Add 40 µl of Sodium phosphate/EDTA Teen buffer to each of the capped tubes containing a filter and beads. Screw cap tightly.

2. Insert tubes one at a time into the bead beater.

3. Bead beat the capped tube for 3 minutes and a speed of 5000 rpm.

4. Remove capped tube from bead beater and place the tube on ice for a minimum of 2 minutes to cool.

5. Wash Steps.
 Spin capped filter tubes for 10 seconds (pulse spin) in microcentrifuge.

Transfer approximately 400 µl of the supernatant to the yellow top filter collection tube.

Spin the yellow top filter tube with the supernatant @ 7000 rpm for 3 minutes.

Transfer the filtered liquid to a blue microcon filter on collection tube #1.

Spin @ 7000 rpm for 1 minute. Check fluid level in the blue microcon filter. If it is above the white base, pulse spin for about 10 seconds to bring the level at or a little below the white area. Several pulse spins may be necessary to bring the level down. This is approximately 100-200 µl of liquid.

Transfer this liquid on the top of the filter to a second blue microcon filter on a clean collection tube #2. Tilt the tube at a 45° C. angle and take off the liquid—do NOT vacuum the filter.

Add 400 µl of PCR water to the second blue microcon filter with the added liquid.

Spin @ 7000 rpm for 2 minutes. Do not be spin dry; approximatley 50-100 µl of liquid should be on top of the filter. Pulse spin if the level is too high Using clean, metal forceps remove the blue microcon filter from the collection tube #2 and place the blue microcon filter on a clean collection tube #3. Discard collection tube #2.

Add 400 µl PCR water to the blue microcon filter on collection tube #3.

Spin @ 7000 rpm for 2 minutes. Do not be spin dry; approximately 50-100 µl of liquid should be on top of the filter. Pulse spin if the level is too high.

Remove the blue microcon filter. Place the blue microcon filter on collection tube #4. Discard collection tube #3

Add 400 µl PCR water to the blue microcon filter on collection tube #4.

Spin for 1 minute @ 7000 rpm. Check fluid level in the blue microcon filter. If it is above the white base, pulse spin for about 10 seconds to bring the level at or a little below the white area. Several pulse spins may be necessary. If the level of liquid is at or a little below the white base, there is approximately 100-200 µl of DNA extract.

If for some reason the pulse spin has brought the level of DNA extract down too low add 200 µl PCR water and bring the level carefully to the white base level by pulse spinning for less time.

Transfer the liquid on the top of the blue microcon filter (i.e., the DNA extract) to the eppendorf tube.

If the PCR assay cannot be performed immediately, keep extract refrigerated.

PCR Assay:

1. Thaw on ice each set of primer/probe/Taq polymerase sets. Once thawed PCR assay must begin. Do NOT refreeze. Keep on ice while testing.

2. Add 20 µl of each of the PCR reaction mixes for each amplicon and one inhibitory control to the appropriately labeled Cepheid reaction tubes; e.g. 1-1A is for amplicon 1, filter 1, a set of primers, probe, Taq polymerase.
   a. Add 5 µl of DNA extract to each of the tubes-rinse tip 1-2 times in the mix and discard the tip.
   b. Use a clean tip for each reaction tube.
   c. Each tube should have a total of 25 µl.

3. Add 15 µl of PCR reaction inhibitory mix to appropriately labeled Cepheid tubes; e.g., INHIB.
   a. Add 5 µl DNA extract to each tube-rinse tip 1-2 times in the mix and discard tip.
   b. Add 5 µl of DNA inhibitory control to each tube-rinse tip 1-2 times in the mix and discard the tip.
   c. Use a clean tip for each reaction tube.
   d. Each tube should have a total of 25 µl.

4. Include as controls:
   NTC (no template control) for each set of primers/probe, Taq.

5. Spin Cepheid tubes in Cepheid microfuge for about 4 seconds. This mixes the PCR reaction mix and DNA into the optic diamond area. Check to see that the optic area is filled.

6. Run Cepheid Smart Cycler

7. Record all CT values (including 0) on the result sheet for the appropriate organism and filter. CT values equal to 34 to 35 indicate negative readings—no *Brucella* detected. CT values below 34 indicate a positive reading—*Brucella* DNA detected.

Table 1 shows the results of assay runs that were performed using the above described protocol. An assay set containing the primers and probe for each amplicon sequence was added to a sample containing either *Brucella melintensis* DNA, the most prevalent strain of the bacterium, or an environmental soil sample. The environmental soil samples were used as controls to demonstrate that the primers and probes derived from the *Brucella* specific amplicon could identify the *Brucella* bacterium, thereby demonstrating the specificity of the amplicon sequence. The *Brucella melintensis* DNA was obtained from American Type Culture Collection. The assay sets containing the probes and primers were obtained from various vendors such as ABI and Biosearch.

The results show that the assay runs having the *Brucella melintensis* DNA in the sample had positive results, CT values of less than 34. Those assay runs with environmental soil samples had negative results, CT values of 34 to 35, an expected result given that *Brucella* bacterium would not be expected to be present in a soil sample. These results show that the primers and probes derived from the *Brucella* specific amplicon can distinguish between DNA from the *Brucella* bacterium and DNA that may be contained in environmental soil samples, thereby, demonstrating that the nucleotide sequences in the amplicons are specific to *Brucella* and that false positive results should not occur using these assays in the field.

TABLE 1

| Negative Control Sequence ID No. | Davis soil D000401 | Davis soil D000402 | Davis soil D000404 | Davis D000405 | Davis D000406 | Davis D000407 | Davis D000408B | Davis D000411 | Davis D000412 | St. Louis MO D000004 | Long Island NY D000019 |
|---|---|---|---|---|---|---|---|---|---|---|---|
| br.ab.C115.1: Seq. ID No. 1, 2, 3 | 35 | 35 | 35 | 35 | 35 | 35 | 35 | 35 | 35 | 35 | 35 |
| br.ab.C88.1: Seq. ID No. 5, 6, 7 | 35 | 35 | 35 | 35 | 35 | 35 | 35 | 35 | 32.7 | 35 | 35 |
| br.ab.C88.4: Seq. ID No. 9, 10, 11 | 35 | 35 | 35 | 35 | 35 | 35 | 35 | 35 | 35 | 35 | 35 |

TABLE 1-continued

| | | | | | | | | | | | |
|---|---|---|---|---|---|---|---|---|---|---|---|
| br.ab.C115.4:<br>Seq. ID No.<br>13, 14, 15 | 35 | 35 | 35 | 35 | 35 | 35 | 35 | 35 | 35 | 35 | 35 |
| br.ab.C123.1:<br>Seq. ID No.<br>17, 18, 19 | 35 | 35 | 35 | 35 | 35 | 35 | 35 | 35 | 35 | 35 | 35 |
| br.ab.C2.1:<br>Seq. ID No.<br>21, 22, 23 | 35 | 35 | 35 | 35 | 35 | 35 | 35 | 35 | 35 | 35 | 35 |

| Brucella<br>Negative Control<br>Sequence ID No. | Columbus<br>OH<br>D000024 | Birmingham<br>AL<br>D000028 | San Jose<br>CA<br>D000036 | Norfolk<br>VA<br>D000051 | Virginia<br>Beach VA<br>D000052 | Atlanta<br>GA<br>D000054 | Baltimore<br>MD<br>D000062 | Brighton<br>MA<br>D000064 | Seattle<br>WA<br>D000068 | Pittsburgh<br>PA<br>D000076 |
|---|---|---|---|---|---|---|---|---|---|---|
| br.ab.C115.1:<br>Seq. ID No. 1, 2, 3 | 35 | 35 | 35 | 35 | 35 | 35 | 35 | 35 | 35 | 35 |
| br.ab.C88.1:<br>Seq. ID No. 5, 6, 7 | 35 | 35 | 35 | 35 | 35 | 35 | 35 | 35 | 35 | 35 |
| br.ab.C88.4:<br>Seq. ID No. 9, 10, 11 | 35 | 35 | 35 | 35 | 35 | 35 | 35 | 35 | 35 | 35 |
| br.ab.C115.4:<br>Seq. ID No. 13, 14, 15 | 35 | 35 | 35 | 35 | 35 | 35 | 35 | 35 | 35 | 35 |
| br.ab.C123.1:<br>Seq. ID No. 17, 18, 19 | 35 | 35 | 35 | 35 | 35 | 35 | 35 | 35 | 35 | 35 |
| br.ab.C2.1:<br>Seq. ID No. 21, 22, 23 | 35 | 35 | 35 | 35 | 35 | 35 | 35 | 35 | 35 | 35 |

| Sequence ID No. | DNA | CT | F.I.R. | CT | F.I.R. |
|---|---|---|---|---|---|
| br.ab.C115.1.F: Seq. ID No. 1, 2, 3 | *B. melintensis* (5 ng total) | 19.7 | 200-550 | 19.67 | 80-280 |
| br.ab.C115.1.F: Seq. ID No. 1, 2, 3 | *B. melintensis* (5 ng total) | 19.61 | 200-550 | 19.6 | 80-280 |
| br.ab.C88.1: Seq. ID No. 5, 6, 7 | *B. melintensis* (5 ng total) | 20.62 | 550-950 | 20.31 | 250-550 |
| br.ab.C88.1: Seq. ID No. 5, 6, 7 | *B. melintensis* (5 ng total) | 20.52 | 550-1000 | 20.58 | 250-550 |
| br.ab.C88.4: Seq. ID No. 9, 10, 11 | *B. melintensis* (5 ng total) | 20.26 | 700-1100 | 20.38 | 300-700 |
| br.ab.C88.4: Seq. ID No. 9, 10, 11 | *B. melintensis* (5 ng total) | 19.79 | 650-1050 | 20.28 | 300-650 |
| br.ab.C115.4: Seq. ID No. 13, 14, 15 | *B. melintensis* (5 ng total) | 19.42 | 600-1050 | 19.61 | 250-600 |
| br.ab.C115.4: Seq. ID No. 13, 14, 15 | *B. melintensis* (5 ng total) | 19.44 | 600-1000 | 19.82 | 250-550 |
| br.ab.C123.1: Seq. ID No. 17, 18, 19 | *B. melintensis* (5 ng total) | 20.01 | 150-450 | 20.48 | 140-230 |
| br.ab.C123.1: Seq. ID No. 17, 18, 19 | *B. melintensis* (5 ng total) | 19.84 | 150-450 | 20.15 | 70-230 |
| br.ab.C2.1: Seq. ID No. 21, 22, 23 | *B. melintensis* (5 ng total) | 20.57 | 400-750 | 20.78 | 200-480 |
| br.ab.C2.1: Seq. ID No. 21, 22, 23 | *B. melintensis* (5 ng total) | 20.65 | 400-750 | 20.91 | 200-500 |

Taqman PCR Conditions:

Gibco/BRL PLATINUM TAQ cat#10966-034(Buffer Mg; 50 mM Mg)

Dntp=Amersham/Pharmacia

| Components: | 1× | Cycling<br>Condition:<br>95° C. | Cepheid Smart<br>Cycler:<br>60 secs. |
|---|---|---|---|
| dH20 | 11.75 | | |
| 10× Buffer | 2.5 | 96° C. | 15 secs |
| 50 mM Mg | 3 | 60° C. | 15 secs 35×. |
| 10 mM dntp | 0.5 | | |
| 10 uM F primer | 0.5 | | |
| 10 uM R primer | 0.5 | | |
| 10 uM/5 uM TaqMan probe | 1 | | |

-continued

| Components: | 1× | Cycling<br>Condition:<br>95° C. | Cepheid Smart<br>Cycler:<br>60 secs. |
|---|---|---|---|
| 5 u/ul Taq(Platinum) | 0.25 | | |
| dna (1 ng/ul) | 5 | | |
| | 25 ul | | |

The inventions disclosed herein are based on nucleotide sequences that are specific to *Brucella*. Accordingly, although air monitors are an effective method of obtaining samples for analyses, a wide variety of other media and methods may be used to provide the samples for analysis for the *Brucella* bacterium and this invention is not limited by the method or media from which a sample for analysis is obtained.

The invention claimed is:

1. A set of polynucleotides comprising a first isolated polynucleotide and a second isolated polynucleotide, wherein the first isolated polynucleotide consists of SEQ ID NO: 4 or the complement thereof and the second isolated polynucleotide consists of SEQ ID NO: 8 or the complement thereof.

2. The set of polynucleotides of claim 1, further comprising at least one isolated polynucleotide consisting of the nucleic acid sequence selected from the group consisting of SEQ ID NOS: 12, 16, 20, and 24 or the complement thereof.

3. The set of polynucleotides of claim 2, comprising six isolated polynucleotides each consisting of one of SEQ ID NOS: 4, 8, 12, 16, 20, and 24 or the complements thereof.

4. The set of polynucleotides of claim 1, further comprising at least one isolated polynucleotides consisting of the nucleic acid sequence selected from the group consisting of SEQ ID NOS: 1, 2, 3, 5, 6, and 7.

5. The set of polynucleotides of claim 2, further comprising at least one isolated polynucleotide consisting of the nucleic acid sequence selected from the group consisting of SEQ ID NOS: 1, 2, 3, 5, 6, 7, 9, 10, 11, 13, 14, 15, 17, 18, 19, 21, 22,and 23.

6. A method for detection of *Brucella melintensis* in a sample comprising:

(i) providing a sample;

(ii) performing a PCR assay to detect the set of polynucleotides of claim 1, in the sample, wherein the detection of a first isolated polynucleotide and a second isolated polynucleotide indicates the presence of *Brucella melintensis* in the sample, wherein the first isolated polynucleotide consists of SEQ ID NO: 4 or the complement thereof and the second isolated polynucleotide consists of SEQ ID NO: 8 or the complement thereof.

7. The method of claim 6 wherein said PCR assay comprises standard PCR.

8. The method of claim 7, wherein said standard PCR comprises fluorogenic 5' nuclease PCR assay.

9. The method of claim 6, wherein said assay is performed using a first forward primer consisting of SEQ ID NO: 1, a first reverse primer consisting of SEQ ID NO:2, and a first hybridization probe consisting of SEQ ID NO:3 for detection of SEQ ID NO:4 and using a second forward primer consisting of SEQ ID NO:5, a second reverse primer consisting of SEQ ID NO:6, and a second hybridization probe consisting of SEQ ID NO:7 for detection of SEQ ID NO:8. and detecting the presence of SEQ ID NO:4 and SEQ ID NO:8 by flurogenic 5' nuclease PCR assay, wherein the presence of SEQ ID NO:4 and SEQ ID NO:8 indicates the presence of *Brucella melintensis* in the sample.

* * * * *

SEQUENCE LISTING

```
<160> NUMBER OF SEQ ID NOS: 24

<210> SEQ ID NO 1
<211> LENGTH: 26
<212> TYPE: DNA
<213> ORGANISM: Brucella sp.
```

<400> SEQUENCE: 1
agcataatcg tcaaaggaaa atatcc                                           26

<210> SEQ ID NO 2
<211> LENGTH: 27
<212> TYPE: DNA
<213> ORGANISM: Brucella

<400> SEQUENCE: 2
agttactttt ctgacgacga cttaacc                                          27

<210> SEQ ID NO 3
<211> LENGTH: 26
<212> TYPE: DNA
<213> ORGANISM: Brucella

<400> SEQUENCE: 3
cgacagctat tatctgctcg tcgcgg                                           26

<210> SEQ ID NO 4
<211> LENGTH: 184
<212> TYPE: DNA
<213> ORGANISM: Brucella

<400> SEQUENCE: 4
agcataatcg tcaaaggaaa atatccaaag gaattacttg agataagcat cgatcgtccc      60
ggcttgtcga tgggtttatt tcaaattcaa taataggtgc gacagctatt atctgctcgt    120
cgcggagatg cagatgatta atcagattgc ttatgctggt taagtcgtcg tcagaaaagt    180
aact                                                                 184

<210> SEQ ID NO 5
<211> LENGTH: 25
<212> TYPE: DNA
<213> ORGANISM: Brucella

<400> SEQUENCE: 5
agcaacgtca ggatctaaca atagg                                            25

<210> SEQ ID NO 6
<211> LENGTH: 26
<212> TYPE: DNA
<213> ORGANISM: Brucella

<400> SEQUENCE: 6
cgtaatgaac tgttccgtca atattg                                           26

<210> SEQ ID NO 7
<211> LENGTH: 27
<212> TYPE: DNA
<213> ORGANISM: Brucella

<400> SEQUENCE: 7
ctcggacaac gattctatgt cgatgcc                                          27

<210> SEQ ID NO 8
<211> LENGTH: 196
<212> TYPE: DNA
<213> ORGANISM: Brucella

<400> SEQUENCE: 8
agcaacgtca ggatctaaca ataggaagtg aagcccgtgt acacgatccg catcatgaac      60

-continued

```
tgtgcctttt ttgcgcatca cggtgtcttc gatgaagaac acaagctcgg acaacgattc    120
tatgtcgatg ccgttctgga tgttgatgag ggcaactcgc tggaaagcga caatattgac    180
ggaacagttc attacg                                                    196

<210> SEQ ID NO 9
<211> LENGTH: 21
<212> TYPE: DNA
<213> ORGANISM: Brucella

<400> SEQUENCE: 9
aggaagtgaa gcccgtgtac a                                               21

<210> SEQ ID NO 10
<211> LENGTH: 21
<212> TYPE: DNA
<213> ORGANISM: Brucella

<400> SEQUENCE: 10
aacggcatcg acatagaatc g                                               21

<210> SEQ ID NO 11
<211> LENGTH: 28
<212> TYPE: DNA
<213> ORGANISM: Brucella

<400> SEQUENCE: 11
tcttcgatga agaacacaag ctcggaca                                        28

<210> SEQ ID NO 12
<211> LENGTH: 113
<212> TYPE: DNA
<213> ORGANISM: Brucella

<400> SEQUENCE: 12
aggaagtgaa gcccgtgtac acgatccgca tcatgaactg tgcctttttt gcgcatcacg     60
gtgtcttcga tgaagaacac aagctcggac aacgattcta tgtcgatgcc gtt           113

<210> SEQ ID NO 13
<211> LENGTH: 20
<212> TYPE: DNA
<213> ORGANISM: Brucella

<400> SEQUENCE: 13
caggttccgc gctttttaag                                                 20

<210> SEQ ID NO 14
<211> LENGTH: 24
<212> TYPE: DNA
<213> ORGANISM: Brucella

<400> SEQUENCE: 14
ctttttattg ttggaaacgg cttt                                            24

<210> SEQ ID NO 15
<211> LENGTH: 32
<212> TYPE: DNA
<213> ORGANISM: Brucella

<400> SEQUENCE: 15
cagcaaagtc ggtatatcgt gtcttcaatc cg                                   32
```

-continued

<210> SEQ ID NO 16
<211> LENGTH: 91
<212> TYPE: DNA
<213> ORGANISM: Brucella

<400> SEQUENCE: 16
caggttccgc gctttttaag tactcagcaa agtcggtata tcgtgtcttc aatccgtggt 60
ggatatcaaa gccgtttcca acaataaaaa g 91

<210> SEQ ID NO 17
<211> LENGTH: 21
<212> TYPE: DNA
<213> ORGANISM: Brucella

<400> SEQUENCE: 17
tccgtcaaga gcgatattgt g 21

<210> SEQ ID NO 18
<211> LENGTH: 27
<212> TYPE: DNA
<213> ORGANISM: Brucella

<400> SEQUENCE: 18
gctattcata atttagggca taatcca 27

<210> SEQ ID NO 19
<211> LENGTH: 19
<212> TYPE: DNA
<213> ORGANISM: Brucella

<400> SEQUENCE: 19
cgccgtcgct tcattccgg 19

<210> SEQ ID NO 20
<211> LENGTH: 128
<212> TYPE: DNA
<213> ORGANISM: Brucella

<400> SEQUENCE: 20
tccgtcaaga gcgatattgt gtggcagtca ctacagccca gctgtttagt cctgtcattt 60
tatttcaagc atgatcctga tcgccgtcgc ttcattccgg ctggattatg ccctaaatta 120
tgaatagc 128

<210> SEQ ID NO 21
<211> LENGTH: 19
<212> TYPE: DNA
<213> ORGANISM: Brucella

<400> SEQUENCE: 21
ggcacggaag accctcact 19

<210> SEQ ID NO 22
<211> LENGTH: 22
<212> TYPE: DNA
<213> ORGANISM: Brucella

<400> SEQUENCE: 22
tcggaaccgc tctatctctt tg 22

-continued

```
<210> SEQ ID NO 23
<211> LENGTH: 27
<212> TYPE: DNA
<213> ORGANISM: Brucella

<400> SEQUENCE: 23
ctgcgtcaga gcatttccag caaaagt                                          27

<210> SEQ ID NO 24
<211> LENGTH: 139
<212> TYPE: DNA
<213> ORGANISM: Brucella sp.

<400> SEQUENCE: 24
ggcacggaag accctcactt tattatctat agccgtgcat tcccgatgct ttaccgctgc      60
gtcagagcat ttccagcaaa agtgcgaagc ggttttgcgt cggataatgc gacaaaacaa     120
agagatagag cggttccga                                                  139
```